United States Patent [19]
Collier

[11] Patent Number: 5,357,784
[45] Date of Patent: Oct. 25, 1994

[54] LUBRICATED FLOW ELONGATIONAL RHEOMETER

[75] Inventor: John R. Collier, Baton Rouge, La.

[73] Assignee: Board of Supervisors of Louisiana State University and Agricultural and Mechanical College, Baton Rouge, La.

[21] Appl. No.: 101,982

[22] Filed: Aug. 4, 1993

[51] Int. Cl.$^5$ ............................................. G01N 11/08
[52] U.S. Cl. ................................................. 73/54.14
[58] Field of Search ............................ 73/54.14, 54.11

[56] References Cited

U.S. PATENT DOCUMENTS

H93  7/1986  Matta et al. ...................... 73/54.11

OTHER PUBLICATIONS

H. C. Kim et al., "Polymer melt lubricated flow elongational rheology I. Newtonian" (to be published 1993; not prior art to this invention).
J. R. Collier et al., "Polymer Melt Elongational Rheology" (1993, unpublished) (not prior art to this invention).
Chatraei et al., "Lubrication squeezing flow: a new biaxial extensional rheometer," J. Rheol., vol. 25, No. 4, pp. 433–443 (1981).
H. C. Kim, *Melt Elongational Flow Rheometry in Converging Channels*, PhD Dissertation, Louisiana State University (defended Jun. 1993, not yet catalogued and shelved by Louisiana State University's Library).
Binding et al., "On the interpretation of data from converging flow rheometers," Rheol. Acta., vol. 28, pp. 215–222 (1989).
J. R. Collier et al., "Lubricated Flow Polymer Melt Elongational Rheometry," abstract in *Theoretical and Applied Rheology*, Proceedings of the 11th International Conference on Rheology, Brussels (Aug. 17–21, 1992)(not prior art to this invention).
Jones, "On the extensional viscosity of mobile polymer solutions," Rheol. Acta, vol. 26, pp. 20–30 (1987).
Zahorski, "The converging flow rheometer reconsidered: an example of flow with dominating extension," J. Non–Newtonian Fluid Mech., vol. 41, pp. 309–322 (1992).
James, "Flow in a converging channel at moderate Reynolds numbers," A.I.Ch.E.J., vol. 37, No. 1, pp. 59–64 (1991).
Williams et al., "On the planar extensional viscosity of mobile liquids," J. Non–Newtonian Fluid Mechanics, vol. 19, pp. 53–80 (1985).
Meissner, "Rheometer zur Untersuchung der deformationsmechanischen Eigenschaften von Kunstoff-Schmelzen unter definierter Zugbeanspruchung," Rheol. Acta, vol. 8, No. 1, pp. 78–88 (1969).
Meissner, "Dehnungsverhalten von Polyäthylen-Schmelzen," Rheol. Acta, vol. 10, No. 2, pp. 230–242 (1971).
Rheometrics data sheet, "RME—Rheometrics elongational rheometer for melts" (1993) (not admitted to be prior art to this application).
H. C. Kim et al., "Polymer melt lubricated flow elongational rheology II. Power Law" (to be published 1993; not prior art to this invention).
A. Pendse et al., "Polymer Melt Lubricated Flow Elongational Rheology III. Rheometer" (unpublished, to be published 1993) (not prior art to this invention).
Crevecoeur et al., "Fibril formation in in situ composites of a thermotropic liquid crystalline polymer in a thermoplastic matrix," J. Appl. Pol. Sci., vol. 49, pp. 839–849 (1993) (not admitted to be prior art).

*Primary Examiner*—Hezron E. Williams
*Assistant Examiner*—Joseph W. Roskos
*Attorney, Agent, or Firm*—John H. Runnels

[57] ABSTRACT

A novel method and apparatus for measuring elongational viscosity are disclosed. It is shown that in a hyperbolic or semi-hyperbolic die geometry with lubricated flow, the elongational viscosity of a fluid can be obtained from pressure drop—flow rate data. Experimental data for polypropylene as core and polyethylene as skin material, and the calculated extensional viscosities are presented. Alternative embodiments of the novel elongational rheometer are described, including alternatives suitable for biaxial flow.

8 Claims, 9 Drawing Sheets

LUBRICATED FLOW ELONGATIONAL RHEOMETER

The development of this invention was partially funded by the Government under grants DMC 8896Q30 and DMR 9202434 awarded by the National Science Foundation. The Government may have certain rights in this invention.

This invention pertains to rheometry, particular to a method and instrument for measuring elongational viscosity.

Rheology is the study of the derogation and flow of matter. A rheometer is a device for measuring the flow of a viscous substance, usually a fluid, for example a poller melt. The viscosity of a substance has two primary components: the shear viscosity and the elongational viscosity. The shear viscosity is the resistance to flow due to a force which is perpendicular to the nodal of the plane on which the force acts. The elongational viscosity is the resistance to flow due to a force which is parallel to the nodal of the plane on which the force acts. The shear viscosity may be thought of as the resistance to fluid flow between layers; and the elongational or extensional viscosity may be thought of as the resistance to stretching of the fluid. As a general proposition, there is little correlation between shear viscosity and elongational viscosity. Knowledge of one does not, in general, allow confident prediction of the other.

Shear rheometry, the measurement of shear viscosity, is a well-developed field. Most current rheometers measure shearing flow. By contrast, extensional or elongational rheometry is still in its formative stages. It is becoming increasingly apparent that extensional flow is important in many industrial applications, including fiber spinning; film casting; extrusion; and the fountain flow of the filling front during injection molding, where the primary flow field is extensional. Improved methods and apparatus for the accurate measurement of the extensional viscosity of processing fluids at operating conditions are highly desirable.

Compared to shear rheometry, the main difficulties in studying the extensional flow of viscoelastic fluids are that (1) it is difficult to generate a steady and controlled elongational flow field, and (2) it is difficult to prevent and/or measure and compensate for the shear effects that typically also occur simultaneously with elongational flow.

Zahorski, "The converging flow rheometer reconsidered: an example of flow with dominating extension," J. Non-Newtonian Fluid Mech., vol. 41, pp. 309–322 (1992) discusses theoretical predictions concerning two-dimensional planar extrusion in a lubricated converging flow rheometer; no experimental data are given. Zahorski states that the flow cannot be expected to be purely extensional—measurable shear effects were said to be certain. Chatraei et al, "Lubricated squeezing flow: a new biaxial extensional rheometer," J. Rheol., vol. 25, no. 4, pp. 433–443 (1981) discloses a lubricated biaxial flow apparatus for measuring elongational viscosity in which a viscous material is compressed between two lubricated disks; no means is disclosed for achieving a constant elongational strain rate. Williams et al., "On the planar extensional viscosity of mobile liquids," J. Non-Newtonian Fluid Mechanics, vol. 19, pp. 53–80 (1985) discloses an instrument for measuring planar extensional viscosity with lubricated converging flow in a hyperbolic planar nozzle. Such a device would primarily be useful for measuring the viscosity of solutions or other relatively low viscosity fluids. The apparatus would not be practical for measurements in high viscosity fluids such as many polymer melts, because a steady flow for such fluids in the planar nozzle would be difficult to achieve. See also Binding et al., "On the interpretation of data from converging flow rheometers," Rheol. Acta, vol. 28, pp. 215–222 (1989); Jones, "On the extensional viscosity of mobile polymer solutions," Rheol. Acta, vol. 26, pp. 20–30 (1987); and James, "Flow in a converging channel at moderate Reynolds numbers," A.I.Ch.E.J., vol. 37, no. 1, pp. 59–64 (1991). In James, there is no mention of lubricated flow; and the application was apparently restricted to solutions, because the Reynolds number was said to be in the range of 100 to 1000. Rheometrics data sheet, "RME - - - Rheometrics elongational rheometer for melts" (1993) (not admitted to be prior art to this application) describes a system for measuring the elongational viscosity of a fluid in which the fluid is supported by a gas stream, and the ends are pulled apart by traction at an exponentially increasing speed; the disclosures of the following two references are similar to that of the Rheometrics data sheet in many respects, except that the fluid was floated on oil rather than supported by a gas stream: Meissner, "Rheometer zur Untersuchung der deformationsmechanischen Eigenschaften yon Kunstoff-Schmelzen unter definierter Zugbeanspruchung," Rheol. Acta, vol. 8, no. 1, pp. 78–88 (1969); and Meissner, "Dehnungsverhalten yon Polyethylen-Schmelzen," Rheol. Acta, vol. 10, no. 2, pp. 230–242 (1971). Crevecoeur et al., "Fibril formation in in situ composites of a thermotropic liquid crystalline polymer in a thermoplastic matrix," J. App. Pol. Sci., vol. 49, pp. 839–849 (1993) (not admitted to be prior art) discloses a trumpet-shaped die for measuring elongational viscosity in polymer melts containing fibers.

These and other problems have been overcome by the present invention of a novel method and apparatus for measuring the elongational viscosity of a fluid. A low viscosity fluid encapsulates a viscous core of the fluid being characterized. The shearing gradient due to confined flow is pushed almost entirely to the low-viscosity skin. The skin and core are forced through an axially symmetric, hyperbolic or "semi-hyperbolic" (or equivalent) die whose shape is designed to generate a constant elongational strain rate in the core fluid, an elongational strain rate which is a linear function of only the flow rate of the core. The elongational viscosity of the core may then be determined by application of momentum balance equations. Alternative dies for measuring both balanced and unbalanced biaxial flow are also described.

A high viscosity material, such as a polymer melt, is caused to flow at a controlled constant strain rate in an essentially pure elongational flow regime, for example inside a die, by using lubricated flow and a hyperbolic or "semi-hyperbolic" surface design. Lubricated flow results from skin/core flow in which the skin has a sufficiently lower viscosity than the core to cause the core to be in essentially pure elongational flow. With a hyperbolic or "semi-hyperbolic" surface, essentially pure elongational flow can be maintained at a steady-state, controlled, constant elongational strain rate. It is preferable to conduct rheological characterization at a steady state, constant elongational strain rate to avoid corrections for other factors, and the complications resulting from such other factors. The value of the strain rate is determined by the specific surface, the volumetric flow rate of the core, and other readily measurable parameters. With a given die, different constant elongational strain rates can be achieved by varying the volumetric flow rate, and the core/skin ratios. A broad range of elongational strain rates can thus be achieved by using a series of dies with different final discharge openings and appropriate die surfaces. Because the flow occurs inside a fixed boundary die, a pressure gradient can be used as the driving force, rather than tensile forces on the ends of test specimens. The imposed pressure gradient can be independently adjusted to control the flow rate for a given combination of skin and core fluids and die geometry.

A "semi-hyperbolic" surface is defined as one in which, for a suitable choice of origin, $r^2z$ is a constant. Put differently, in the direction of the z-axis, the cross-sectional area decreases as z increases, with the area being proportional to $1/z$. Such a surface may be generated, for example, by rotating about the z-axis the curve $r=z^{-0.5}$.

The method and apparatus of the present invention will be useful, for example, in measuring the elongational viscosity of either polymer solutions or of polymer melts. This invention readily lends itself to an attachment for existing rheometers, which typically measure only shear viscosity by flow through a capillary. A conical, semi-hyperbolic die in accordance with the present invention may be attached to many existing rheometers to allow measurement of elongational viscosity, with minimal investment in additional equipment.

Figure 1:
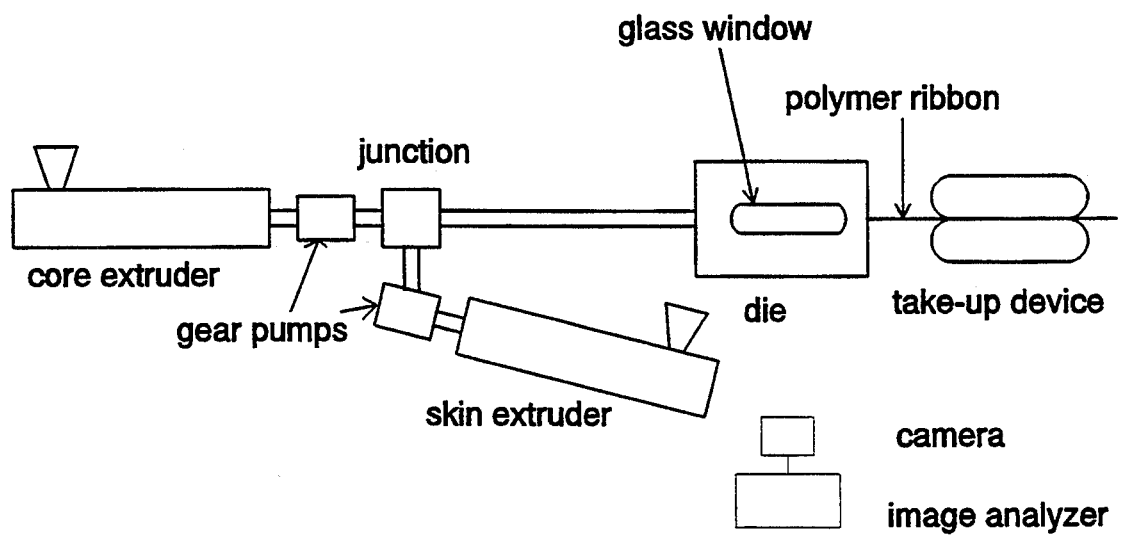
FIG. 1 illustrates the experimental rheometer used to demonstrate the concept.

The flow of the polymer to be characterized should ideally be essentially pure extensional flow. This result may be achieved by maintaining a high Reynolds number in the flow (on the order of 100). The "Reynolds number," a parameter well known in the art, is a dimensionless function of several variables, each of which influences flow behavior of a fluid. In a confined flow, the Reynolds number is the product of a characteristic dimension, the fluid density, and a characteristic velocity; divided by the viscosity of the fluid. In a pipe the characteristic dimension is the pipe's diameter, and the characteristic velocity is the average velocity. If the density and viscosity vary across the pipe, then their average values are used. By collapsing a number of variables affecting flow behavior into a single, dimensionless nun%her, the number of independent variables in the system is reduced, and the characterization is independent of the measurement system (e.g., SI, English) used. A high Reynolds number flow implies that the boundary layer will be thin. But a high Reynolds number flow will often not be possible in the case of polymer melts, where systems typically have low Reynolds numbers (on the order of 0.01 or lower). In other works on polymer solutions, lubricated stagnation flow has been used to provide a planar extensional field in an assembly, and a lubrication approximation was used to determine the planar extensional viscosity of polymer solutions.

Another desired property for a converging-channel-flow extensional (i.e., elongational) rheometer is that the shape of the converging section should be such that the elongational strain rate is constant along the flow direction. A linear converging profile would be unsuitable, because in that geometry the elongational strain rate increases rapidly along the flow direction. A hyperbolic profile following an equation of the form $$x(z) = \frac{B}{z + A} \quad (1)$$

(where A and B are constants) gives a constant elongational strain rate in the flow direction z in a rectangular cross-section die which converges in the dimension of thickness, and has a constant width. The hyperbolic profile may be used in either an (approximately) two-dimensional die or a three dimensional die in the shape of a rotated hyperboloid. The analogous equation for an axially symmetric, conical converging flow is then $$r^2(z) = \frac{C}{z + D} \quad (2)$$

where C and D are constants. Equation 2 defines a semi-hyperbolic surface, or semi-hyperboloid. The strain rate is then $$\dot{\epsilon} = \frac{Q}{2Bw} \quad (3)$$

for channel flow, or $$\dot{\epsilon} = \frac{Q}{\pi C} \quad (4)$$

for axially symmetric flow. In both cases the strain rate is a linear function of only the flow rate of the core polymer and of the design parameters, e.g. the values of B and C. By using different channels over a range of flow rates, a set of channels or dies to measure a range of strain rates can be prepared. As an example embodiment of this invention, an extensional rheometer for polymer melts is described below.

If the skin viscosity is at least a factor of about four smaller than that of the core, the skin will normally encapsulate the core. Therefore when the flow is intentionally layered preceding the measurement zone, an even coating will naturally occur. Although not a requirement, the use of a skin layer that is significantly shear-thinning is beneficial in that not as severe a requirement then exists for the lower viscosity of the skin compared to that of the core.

At low flow and strain rates for a mixed shear and elongational flow (i.e. converging flow in a fixed boundary region), less mismatch of viscosity between the skin and core are needed than at higher rates. If the skin is significantly shear-thinning, its effective viscosity at higher flow rates will be significantly lowered, making it more efficient in localizing shearing effects in the skin and in protecting the core layer. The higher rates are of particular interest, because most industrial processing operations occur at such rates; but current elongational rheometers are not capable of taking measurements at high flow rates.

When a viscous fluid (i.e. a fluid which is not inviscid) flows past a fixed boundary, a shearing velocity gradient develops as the fluid in contact with the boundary sticks to it, or is impeded by it. This shearing velocity gradient causes vorticity or rotational flow to occur. In contrast to shearing flow, pure elongational flow (or extensional flow) is one in which no shearing gradient and therefore no vorticity occurs. Pure elongational flows typically occur when no fixed boundary is present, and the flow rate is not high enough for the fluid phase at the surface to cause significant drag. In polymer processing in air (or in a gas phase) the drag becomes significant only at extremely high draw rates, e.g. thousands of meters a minute. Elongational flows are generally employed to develop orientation, thereby enhancing mechanical properties in polymeric and food products, e.g. textile and industrial fibers, oriented films, noodles, spaghetti, taffy, etc. The presence of a significant shearing gradient tends to be counterproductive in imparting orientation due to the associated vorticity. Therefore these production operations are typically performed in free boundary flow, i.e. outside of a die.

In a skin/core geometry with a sufficiently low skin viscosity, the core is in essentially pure elongational flow, enabling measurements to be made in an enclosed system. An enclosed system, in turn, permits the use of a pressure gradient as the driving force. The pressure gradient can be measured with a series of pressure transducers. If the flow is measured in a die that has a section with glass side windows, the elongational strain rate can be measured by following tracer particles through the observation section of the die with a video system. These results may be examined with an image analysis unit.

In particular, the observation section of a glass-sided, rectangular cross-section die was designed and manufactured to have the converging section geometry controlled by inserts that were machined separately from the die. Therefore the geometry could be changed without much difficulty. To obtain a constant elongational strain rate for a section of the converging region, a hyperbolic-shaped surface insert was used. The level of elongational strain rate is controlled by the actual reduction in cross sectional area of flow (dictated by the inserts), and by the volumetric flow through the die. Therefore a set of die inserts and a series of flow rates can be used to characterize the core material at a series of constant elongational strain rates.

The current device used two plasticating extruders as sources of polymer melts, although pressurized cylinders, pistons in cylinders, or other sources could also be used. The current units are laboratory scale extruders which enabled operations at elongational strain rates analogous to those of polymer and food processing systems.

General Principles

In H. C. Kim et al., "Polymer melt lubricated flow elongational theology I. Newtonian" (to be published 1993; not prior art to this invention); H. C. Kim et al., "Polymer melt lubricated flow elongational rheology II. Power Law" (to be published 1993; not prior art to this invention); H. C. Kim, *Melt Elongational Flow Rheometry in Converging Channels*, PhD Dissertation, Louisiana State University (defended June 1993, not yet; catalogued and shelved by Louisiana State University's library); J. R. Collier et al., "Lubricated Flow Polymer Melt Elongational Rheometry," abstract in *Theoretical and Applied Rheology*, Proceedings of the 11th International Conference on Rheology, Brussels (August 17-21, 1992)(not prior art to this invention); A. Pendse et al., "Polymer Melt Lubricated Flow Elongational Rheology III. Rheometer" (unpublished, to be published 1993)(not prior art to this invention); and J. R. Collier et al., "Polymer Melt Elongational Rheology" (1993, unpublished)(not prior art to this invention), the entire disclosures of each of which are incorporated by reference, it is shown that when two polymers are extruded in a skin/core-type three layer assembly (skin/core/skin) in a converging, rectangular cross-section channel with a hyperbolic profile, an essentially pure extensional flow field is generated in the core polymer if the following conditions are met:

(1) The zero-shear viscosity ratio of the core to skin should be at least about 100.
(2) The ratio of flow rate of the core to the flow rate of the skin should be in the range of at least about 5 to 10.
(3) The two polymer melts should not be miscible.
(4) There should preferably be no crossover between the two curves for viscosity versus shear rate for the skin polymer and the core polymer, respectively. This means that at any shear rate (at least any shear rate within the ranges to be measured), the viscosity of the skin layer should not be greater than the viscosity of the core. This condition is aided if the skin layer is a shear-thinning material, because increasing shear rates would then lower the shear viscosity of the skin, pushing the bulk of the shear gradient to the skin layer.

If the conditions are met, then it has been demonstrated both numerically and experimentally that the core polymer experiences essentially pure elongational flow.

FIG. 1 illustrates the experimental apparatus used. There were two extruders, one extruder for the core, and one extruder for the skin. The melt entered the die, which was equipped with opposing side glass windows to allow observation. Tracer particles may be added to one or both polymers to assist analysis of movement. For example, a computer aided image processor has been used to determine the velocity profile of the core polymer. The flow rates of the skin and core were independently controlled. Because the extrudate was discharged to the atmosphere, the pressure inside the die was taken as the total pressure drop across the die.

The polypropylene used for the experiments was obtained from Phillips (Grade HGY 040). The melting point was measured as 164° C., and the zero-shear viscosity at 200° C. was measured as 77,000 Pa S. The low density polyethylene used was obtained from Dow, and had a melting point of 135° C. and a zero-shear viscosity of 63 Pa S at 200° C. The power law index for polypropylene was 0.91 and that for polyethylene was 0.98.

Theoretical Considerations

The equations for the elongational viscosity of the core and of the skin are solved simultaneously. In the skin, the contributions of both shear and elongational flows are considered. The total pressure drop is assumed to be the same in both the skin and the core. It is also assumed that the skin's shear viscosity skin follows the power law model. The power law model is based on the assumption that the non-Newtonian (e.g, shear-thinning) behavior can be modelled by equating the stress to the strain rate, raised to a power. This power is one for a Newtonian fluid, and is less than one for a shear-thinning fluid. The pressure drop is measured experimentally for several combinations of skin and core flow rates.

Figure 2:
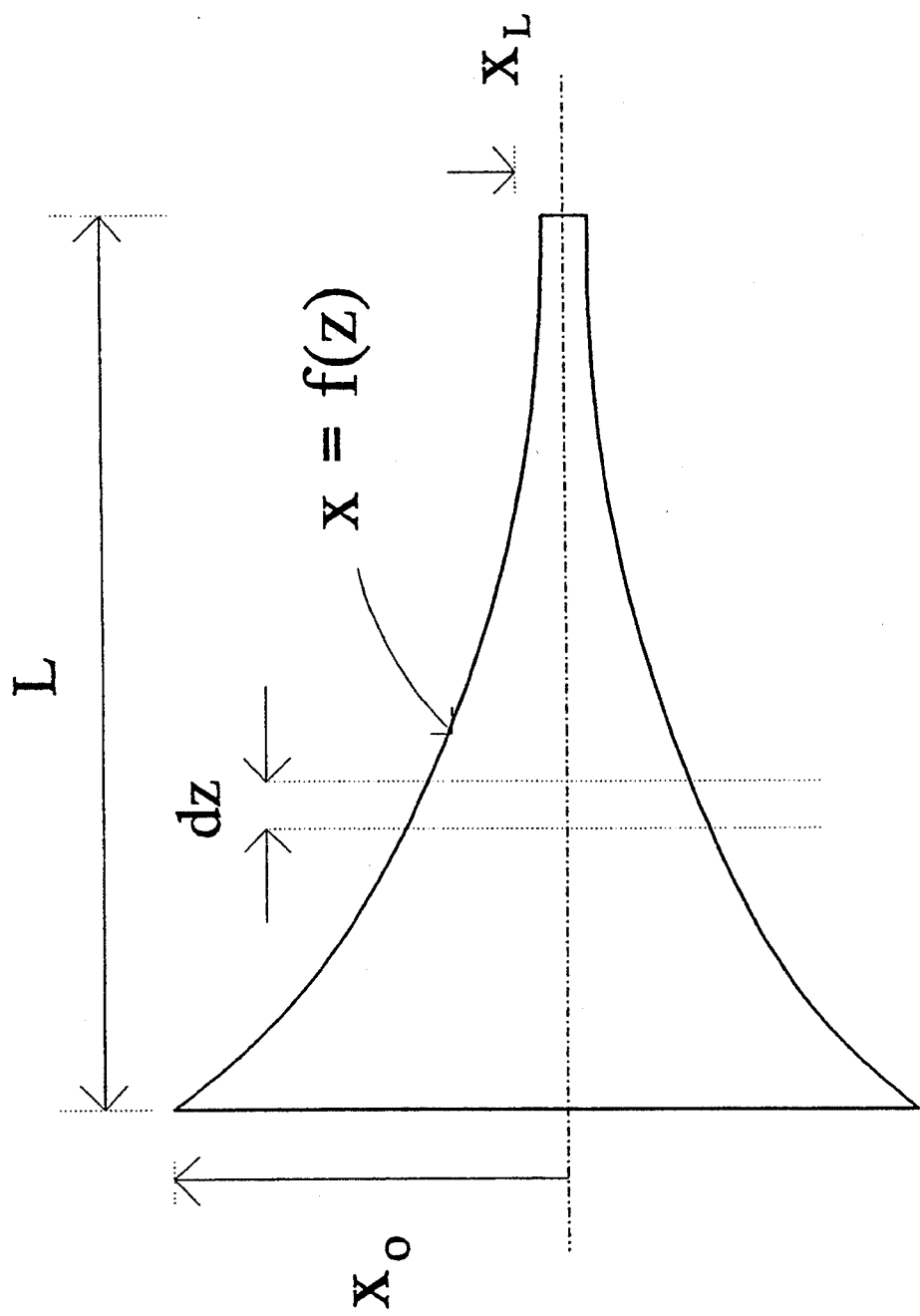
FIGS. 2 and 3 illustrate cross-sections of the die.

The following general assumptions are made:
(1) The two fluids are incompressible.
(2) Steady state flow in the converging channel is considered. Because the width is constant, only the velocity gradients in z and x axes are considered. (See FIG. 2, illustrating a cross-section of the die).
(3) It is assumed that the core flows purely in the elongational mode. The hyperbolic design of the die and the choice of a suitable material for the skin layer permit this assumption to be fulfilled, as experimental data have
(4) The interface between the core and skin follows a streamline contour. (A streamline is a path traced in steady-state flow by particles that start in the same location in the fluid.) (Image analysis has verified this assumption in a number of trials.)
(5) The elongational strain rate is constant. The proper die geometry can ensure that this assumption is satisfied, as has been demonstrated by flow visualization experiments.

The elongational viscosity $\eta$ is defined as $$\eta = \frac{\tau_{zz} - \tau_{xx}}{\dot{\epsilon}} \quad (5)$$

and $$\dot{\epsilon} = \frac{\delta v_z}{\delta z} \quad (6)$$

where $\dot{\epsilon}$ = elongational strain rate.

Determination of $\tau_{zz} - \tau_{xx}$

Using the above assumptions, and applying the momentum equation to the core gives $$\rho v_z \frac{dv_z}{dz} = -\frac{dp}{dz} - \frac{d\tau_{zz}}{dz} \quad (7)$$

$$\rho v_x \frac{dv_x}{dx} = -\frac{dp}{dx} - \frac{d\tau_{xx}}{dx} \quad (8)$$

Integrating in the z direction along the flow direction in the die, from z=0 to z=L, we get:

$$\tau_{zz} = -\Delta P - \rho \int_{v_i}^{v_o} v_z dv_z \quad (9)$$

$$\tau_{zz} = -\Delta P - \frac{\rho}{2} [v_o^2 - v_i^2] \quad (10)$$

where $v_i$ and $v_o$ are the core layer velocities in the z direction at the entry and the exit of the die respectively, and $\Delta P$ is pressure drop in the core.

We now apply the incompressibility equation:

$$\Delta_{zz} + \Delta_{xx} = 0 \quad (11)$$

For generalized Newtonian flow, we know that $$\tau = \eta \Delta \quad (12)$$

where $\eta$ is a scalar parameter which may be a function of $\Delta$. From the above two equations, we can state that $$\tau_{zz} + \tau_{xx} = 0 \quad (13)$$

which leads to $$\tau_{zz} - \tau_{xx} = 2\tau_{zz} \quad (14)$$

Determination of $v_i$ and $v_o$

As discussed above, the converging section profile was machined so that its surface shape was as described in Equation 1. The strain rate $\dot{\epsilon}$ for this profile as a function of the flow rate can be written:

$$\dot{\epsilon} = \frac{Q_c}{2Bw} \quad (15)$$

where $Q_c$ is the flow rate of the core and w is the width of the die. For a given experiment $Q_c$ is held constant. From a mass balance, the velocities in the flow direction can now be computed as $$v_z = \frac{Q_c}{wx} \quad (16)$$

Therefore, $$v_i = \frac{Q_c}{wx_i} \quad (17)$$

and $$v_o = \frac{Q_c}{wx_o} \quad (18)$$

Determination of Elongational Viscosity of the Core

Substituting Eq. 14 and Eq. 15 into Eq. 10, and with simplifying geometric assumptions, $$\tau_{zz} - \tau_{xx} \approx 2\tau_{zz} = -2\Delta P - \rho \dot{\epsilon}^2 \left( L^2 - \frac{B^2}{(L+A)^2} \right) \quad (19)$$

$$= \eta_E{}^C \dot{\epsilon} \quad (20)$$

Rearranging these two equations gives $$\eta_E{}^C = -\frac{\Delta P}{\dot{\epsilon}} - \rho \dot{\epsilon} \left( L^2 - \frac{B^2}{(L+A)^2} \right) \quad (21)$$

Thus Eq. 21 has a convenient form for determining the elongational viscosity ($\eta_E$) of the core polymer melt from the measured pressure drop ($-\Delta P$), known flow rate data ($Q_c$), the elongational strain rate, and the die design parameters (B and L). Note that the die design parameter B is a function of the interface position, and hence of the ratio of the flow rates of the core and skin. The interface position can either be observed experimentally, or it may be calculated from the equations of H. C. Kim et al., "Polymer melt lubricated flow elongational rheology II. Power Law" (to be published 1993; not prior art to this invention). The parameter B can then be calculated using the die profile equation (Eq. 1).

The actual die used had a converging insert with an additional section providing the melt a smooth entry into the converging section. This section contributes to the total pressure drop. From the known dimensions of these die sections, the velocity profiles can be estimated, from which the pressure drops due to these sections can be determined. The total pressure drop is then corrected by subtracting the pressure drops for the entry and exit sections, leaving the net pressure drop from the hyperbolic section alone.

Table I (appearing below) lists actual and corrected pressures from experimental measurements, and the resulting estimated extensional viscosities.

Determination of $\Delta P_S$ in the Skin Layer

The total pressure drop in the skin layer is assumed to be the sum of the pressure drop due to shear flow, $\Delta P_S$ (which is essentially located entirely in the skin), and that due to elongational flow, $\Delta P_E$. These components are assumed to be separable and independent of one other.

To determine the elongational component of the pressure, the shear component of the pressure is subtracted from the total pressure. Determination of the shear component is described below.

Figure 3:
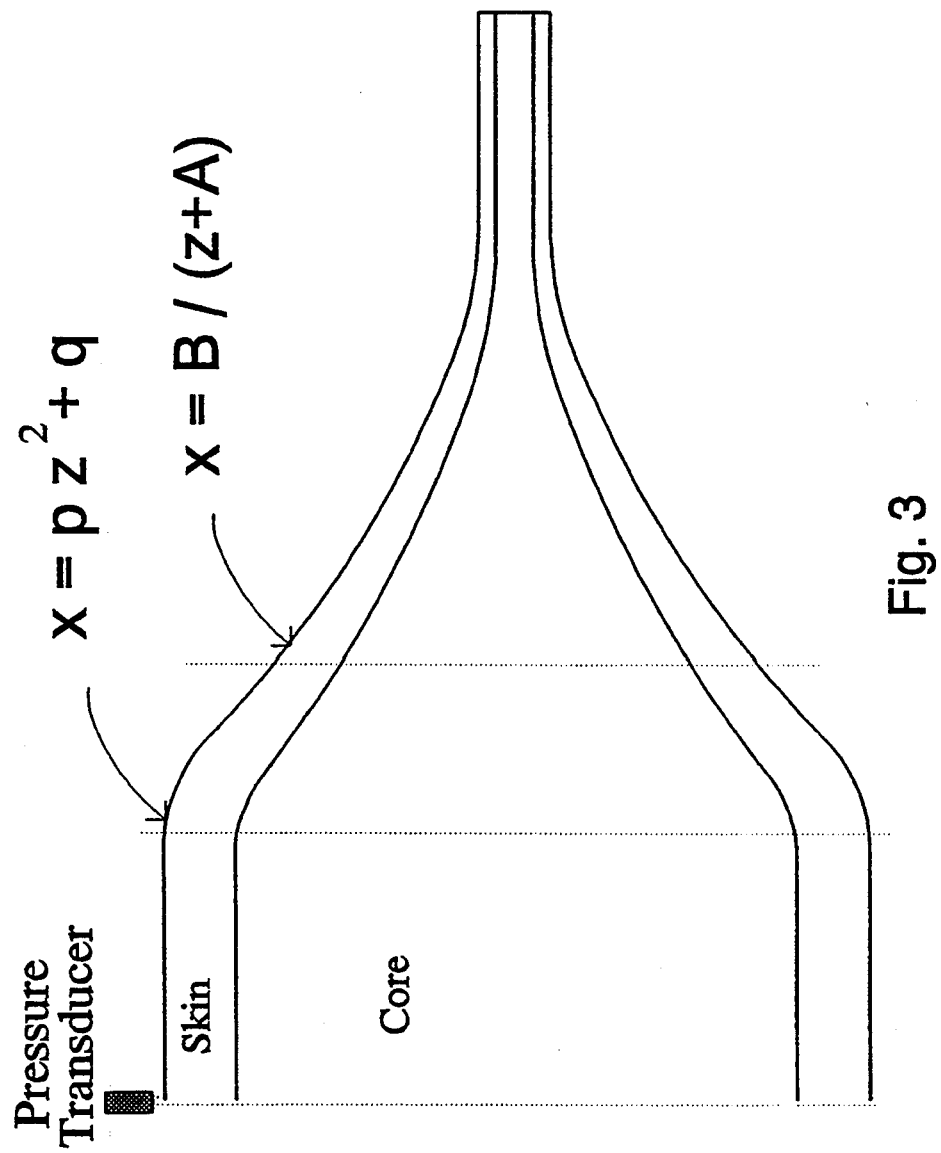

FIG. 3 illustrates a cross section of the die. From a force balance, $$2 dP_S x(1 - \kappa) w = 2\sigma_S \cos(\theta) \, w \frac{dx}{\cos(\theta)} \quad (22)$$

From the power law approximation, $$\rightarrow \quad dP_S = \frac{\sigma_S \, dx}{x(1 - \kappa)} \quad (23)$$

$$\sigma_S = K \dot{\gamma}^n \quad (24)$$

$$\therefore \quad dP_S = \frac{K \dot{\gamma}^n \, dx}{x(1 - \kappa)} \quad (25)$$

Thus the shear component of the flow as a function of the die profile ($x(z)$) and shear strain rate ($\dot{\gamma}$) may be obtained. The die profile is established by the design of a particular die. The shear rate at the wall can be determined if the velocity profile for the skin is known. For the hyperbolic converging flow geometry, the velocity profile for the skin layer in a 3-layer flow in a converging channel is $$v_z = \frac{Q_S \left(1 - \left(\frac{x}{h}\right)^{\frac{1}{n}+1}\right)}{2wh \left[1 - \frac{c}{h} - \left(\frac{1}{2 + 1/n}\right)\left(1 - \frac{c}{h}\right)^{2+\frac{1}{n}}\right]} \quad (26)$$

where c is the interface position and h, is the die wall height from the centerline. The shear rate at the wall ($x = h$) is then $$\dot{\gamma} = \frac{dv_z}{dx}\bigg|_{x=h} = \quad (27)$$

$$\frac{Q_S}{2wh^2 \left[1 - \frac{c}{h} - \left(\frac{n}{2n + 1}\right)\left(1 - \frac{c}{n}\right)^{\frac{2n+1}{n}}\right]}$$

$$\frac{c}{h} = \kappa \text{ (constant)}$$

The assumption that K is a constant is equivalent to assuming that the streamline of the interface doesn't change in the z direction. This is a well-founded assumption, as has been verified by experiment.

Substituting this equation into Eq. 23 gives $$dP_S = \frac{K}{w(1 - \kappa)} \left(\frac{Q_S}{2(1 - \kappa)}\right)^n \frac{dx}{x^{2n+1}} \quad (28)$$

Substituting the equation for the converging die-surface (Eq. 1) in Eq. 28, and integrating from $x=0$ to $x=L$ gives $$\Delta P_S = \frac{K \, Q_S^n}{2^n w B^{2n+1}(1 - \kappa)^{1+n}} \left[\frac{(L + A)^{2n+2} - (A)^{2n+2}}{2n + 2}\right] \quad (29)$$

Determination of $\Delta P_E$ for the Skin Layer

From a force balance, $$\delta P_E W(\kappa - 1)x = \sigma_E \{w(\kappa - 1)(x + \delta x) - w(\kappa - 1)x\} \quad (30)$$

$$\delta P_E = \frac{\sigma_E \, \delta x}{x} \quad (31)$$

$$\sigma_E = \eta_E^S \dot{\epsilon} \quad (32)$$

$$\rightarrow \quad \delta P_E = \frac{\eta_E^S \dot{\epsilon} \, \delta x}{x} \quad (33)$$

Integrating from $y_o$ to $y_L$, $$P_E = \eta_E^S \dot{\epsilon} \ln\left(\frac{x_L}{x_o}\right) \quad (34)$$

$$P_E = \eta_E{}^S \dot{\epsilon} \ln\left(\frac{L+A}{A}\right) \tag{35}$$

Determination of Elongational Viscosity of the Skin

The total pressure drop is now the sum of its two components:

$$\Delta P = \Delta P_s + \Delta P_E \tag{36}$$

Substituting the expressions for $\Delta P_s$ and $\Delta P_s$, $$\Delta P = \frac{K Q_S{}^n}{2^n w B^{2n+1}(1-\kappa)^{1+n}} \left[\frac{(L+A)^{2n+2} - (A)^{2n+2}}{2n+2}\right] + \tag{37}$$

$$\frac{\eta_E{}^S Q_c}{2Bw} \ln\left[\frac{L+A}{A}\right]$$

Equation 37 expresses the pressure drop as a function of the skin and the core flow rates. The only unknown parameter in the above equation is $\eta_E$ for the skin material. By conducting several experiments with different skin/core ratios, the elongational viscosities of skin and the core may be obtained.

Experimental Results and Discussion

Figure 4:
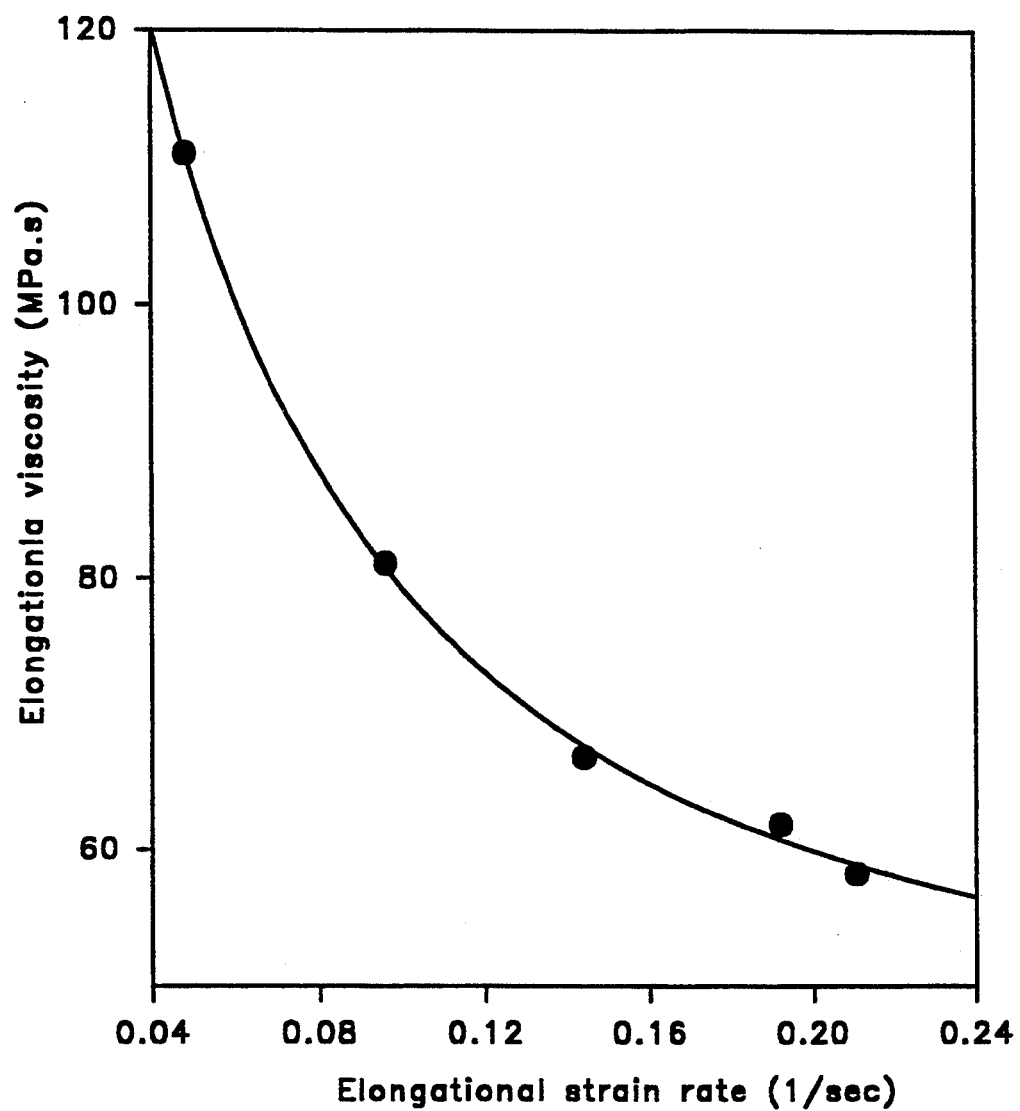
FIG. 4 illustrates a plot of measured elongational viscosity versus elongational strain rate.

Table I lists the experimental data obtained for pressure drop and flow rates of the skin and core, and the calculated elongational viscosities. The measured elongational viscosity is plotted against the elongational strain rate in FIG. 4. The elongational viscosity was seen to decrease as the strain rate increased.

TABLE I

| | | | | | Elongational Viscosity |
|---|---|---|---|---|---|
| $Q_C$ (g/min) | $Q_S$ (g/min) | $\Delta P$ (psi) | Corr $\Delta P_E$ (psi) | Strain Rate (1/S) | $\eta_E$ (Pas) $\times 10^{-7}$ CORE |
| 4.5 | 0.5 | 340 | 262 | 0.04 | 4.695 |
| 9.0 | 1.0 | 520 | 364 | 0.08 | 3.26 |
| 13.5 | 1.5 | 630 | 397 | 0.12 | 2.37 |
| 18.0 | 2.0 | 720 | 409 | 0.16 | 1.83 |
| 8.0 | 2.0 | 480 | 423 | 0.085 | 3.52 |
| 6.4 | 1.6 | 440 | 394 | 0.069 | 4.10 |
| 4.0 | 1.0 | 330 | 301 | 0.04 | 5.02 |
| 2.4 | 0.5 | 240 | 226 | 0.026 | 6.627 |
| 3.0 | 2.0 | 260 | 247 | 0.047 | 3.693 |

The present invention will be compatible with many existing capillary shear rheometers, so that extensive assembly often will not be required to practice the invention in conjunction with such rheometers. For example, an auxiliary unit can be added to an existing capillary melt rheometer without needing elaborate additional apparatus. An accessory for conventional capillary rheometers could readily be made that would allow the novel elongational rheometer of this invention to be used in conjunction with the normal shearing flow measurements made by the capillary system.

The examples discussed above used a side-viewing die fed by a coextrusion system to facilitate measurements to confirm the validity of the underlying theory. A capillary rheometer accessory would more likely have the conical shape of a rotated semi-hyperboloid. Both geometries have surfaces designed to impart constant elongational strain rates. The principles are the same with both geometries. The planar die allowed confirmation of the technique by observing tracer particles. In a conical (i.e., axially symmetric) geometry this observation would be more difficult, but is now unnecessary as the principle underlying this invention has been successfully demonstrated. The conical geometry will typically be preferred, as it would be compatible with existing capillary rheometers used for shearing flow measurements.

The system is flexible. The inserts in the die can be changed easily. A wide range of constant strain rates can be achieved by using appropriate insert profiles in the die and by varying the volumetric flow rate.

The choice of a suitable skin material is important. The conditions discussed above should be met to ensure that the core undergoes essentially pure extensional flow. Although suitable skin materials will depend, to a degree, on the particular core material, materials which will often make good skin materials will include silicone fluids, and high-melt index polymers.

Figure 5A:
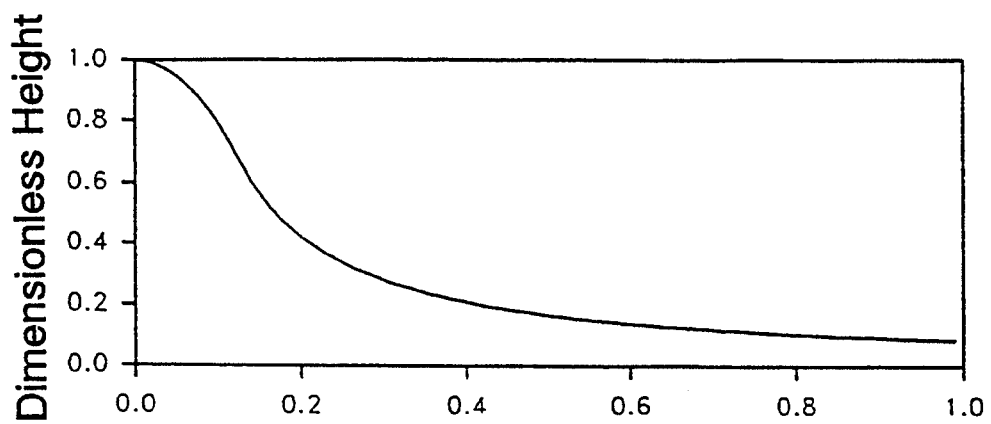
FIGS. 5(a)–5(c) illustrate the shape of the inserts, the predicted core layer elongational strain rate as a function of position, and the corresponding core velocity for a modified hyperbolic die.
Figure 5B:
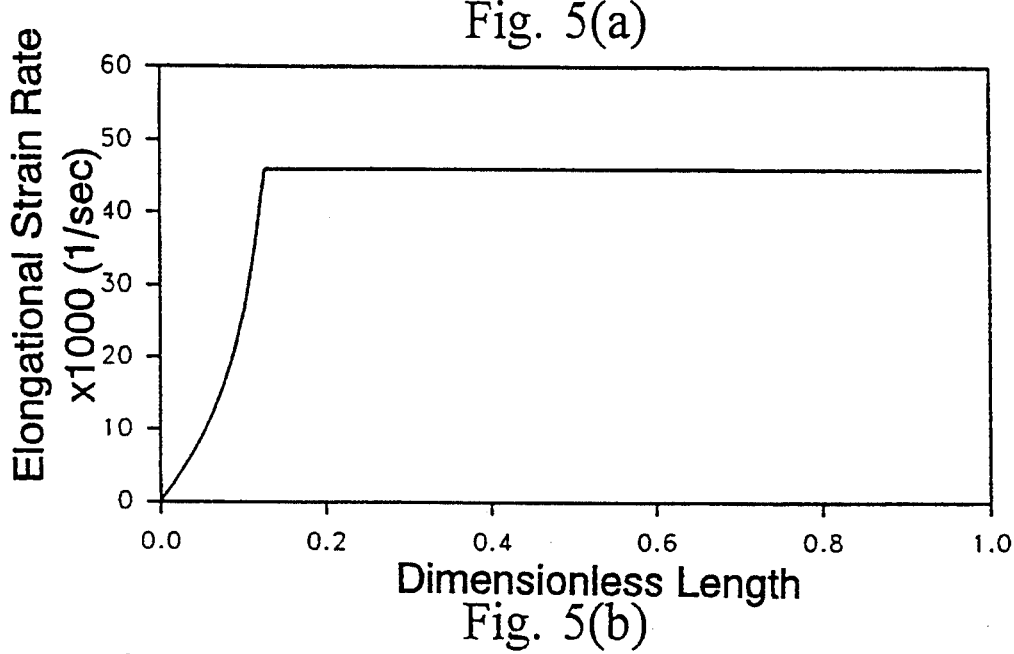
Figure 5C:
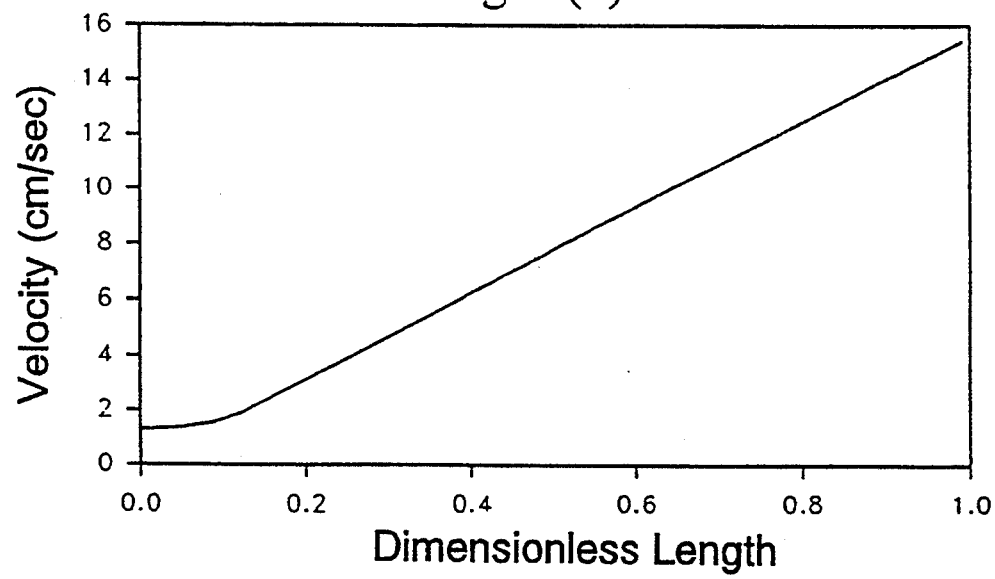
Figure 6:
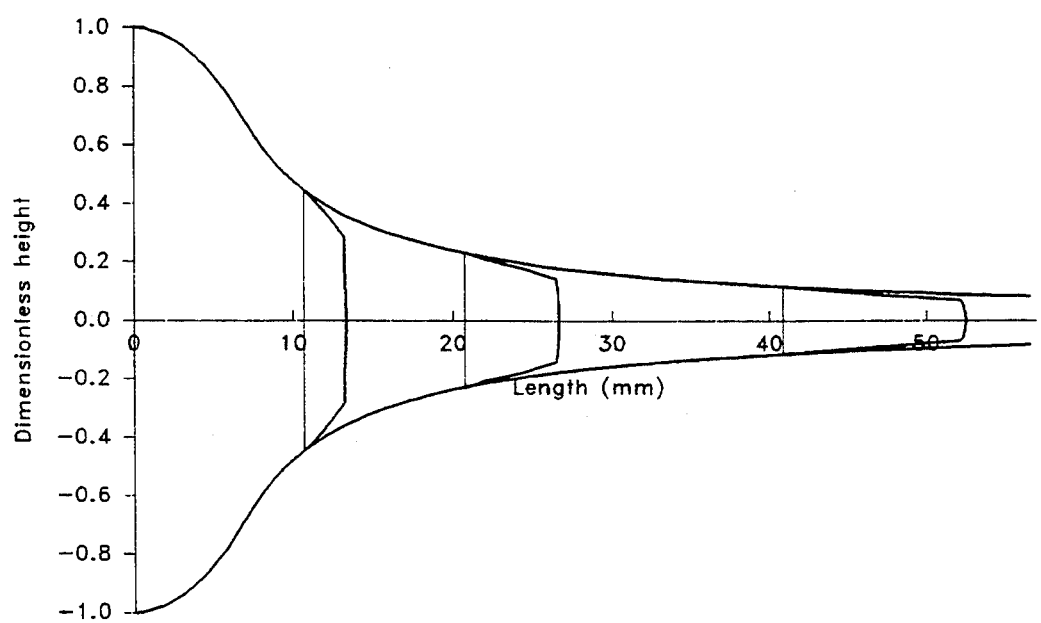
FIG. 6 illustrates predicted velocity profiles for the skin and core at three indicated positions in the measurement section.
Figure 7:
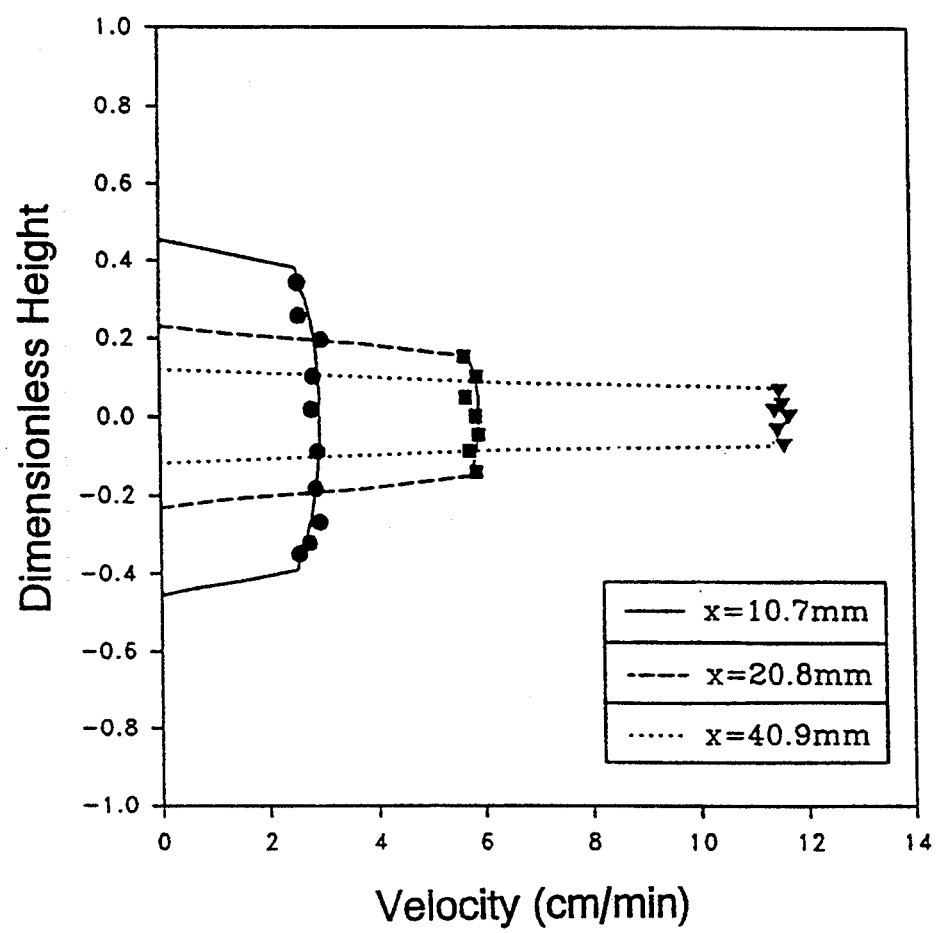
FIG. 7 illustrates agreement between the predicted profiles (lines) and the actual measured velocities of tracer particles for three positions.

It is desirable that the core layer have a constant elongational strain rate in at least a portion of the measurement section, a result which can be achieved with a hyperbolic- or semi-hyperbolic-shaped convergence section. However, such a section standing alone might lead to instabilities in the entrance to the converging flow section, as a step change in the elongational strain rate could be induced. If there is a constant cross-section preceding the entrance, there would be a near-zero elongational strain rate before the entrance, followed by a controlled elongational strain rate in the hyperbolic convergence section. For the examples described above, a modified hyperbolic convergence section was therefore designed and milled. A transition section preceded the measurement section. In the transition section, the elongational strain rate was smoothly increased to the measurement section value rather to avoid a discontinuous change. The shape of the inserts, the predicted core layer elongational strain rate as a function of position, and the corresponding core velocity are illustrated in FIGS. 5(a)–5(c) for this modified hyperbolic die. FIG. 6 illustrates the predicted velocity profiles for the skin and core at three indicated positions in the measurement section. The agreement between the predicted profiles (lines) and the actual measured velocities of tracer particles is shown in FIG. 7 for these three positions. There is excellent agreement between the predicted and actual velocities, demonstrating that the core experienced an essentially constant elongational strain rate in the measurement section.

Figure 8:
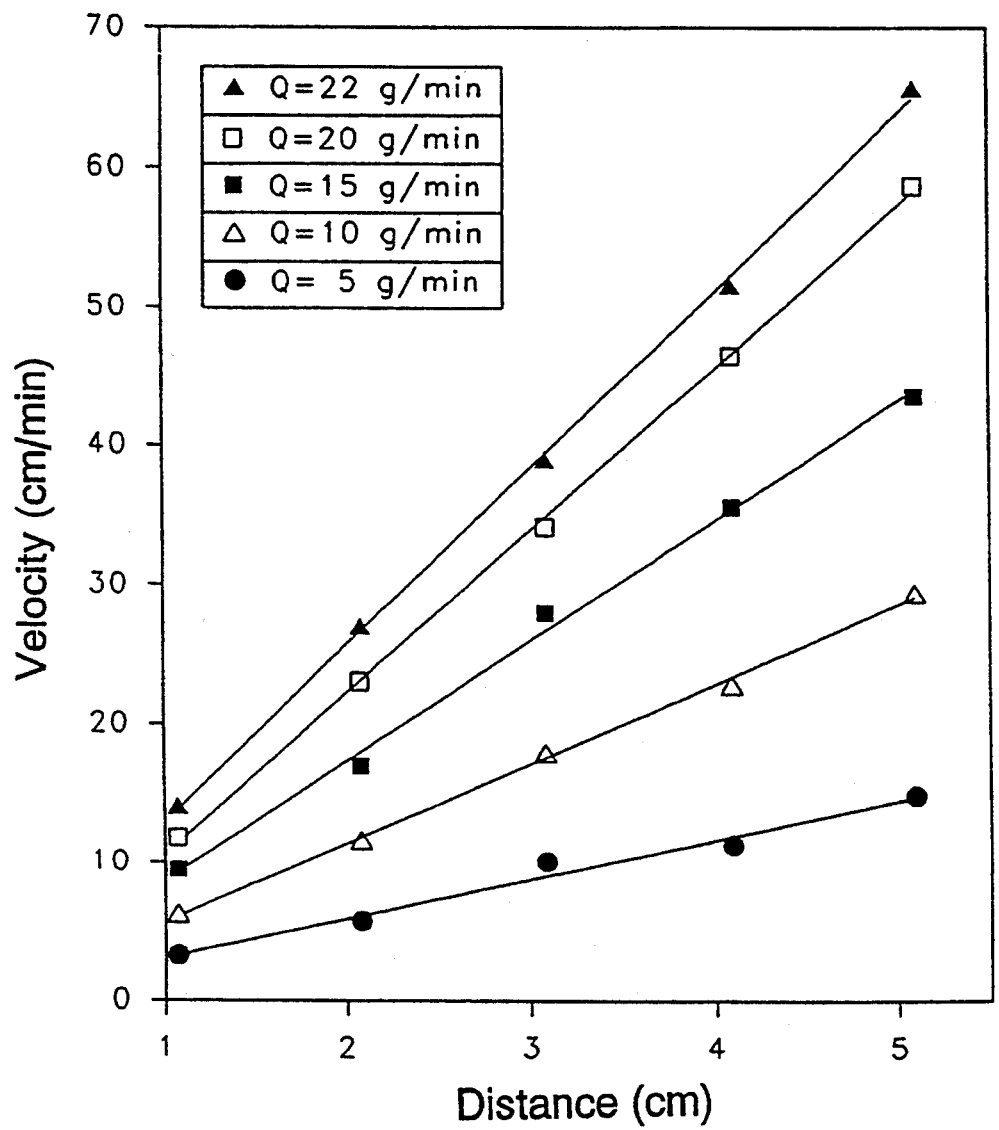
FIG. 8 illustrates measured velocity of tracer particles as a function of position downstream in the hyperbolic section of a die for five different volumetric flow rates.
Figure 9:
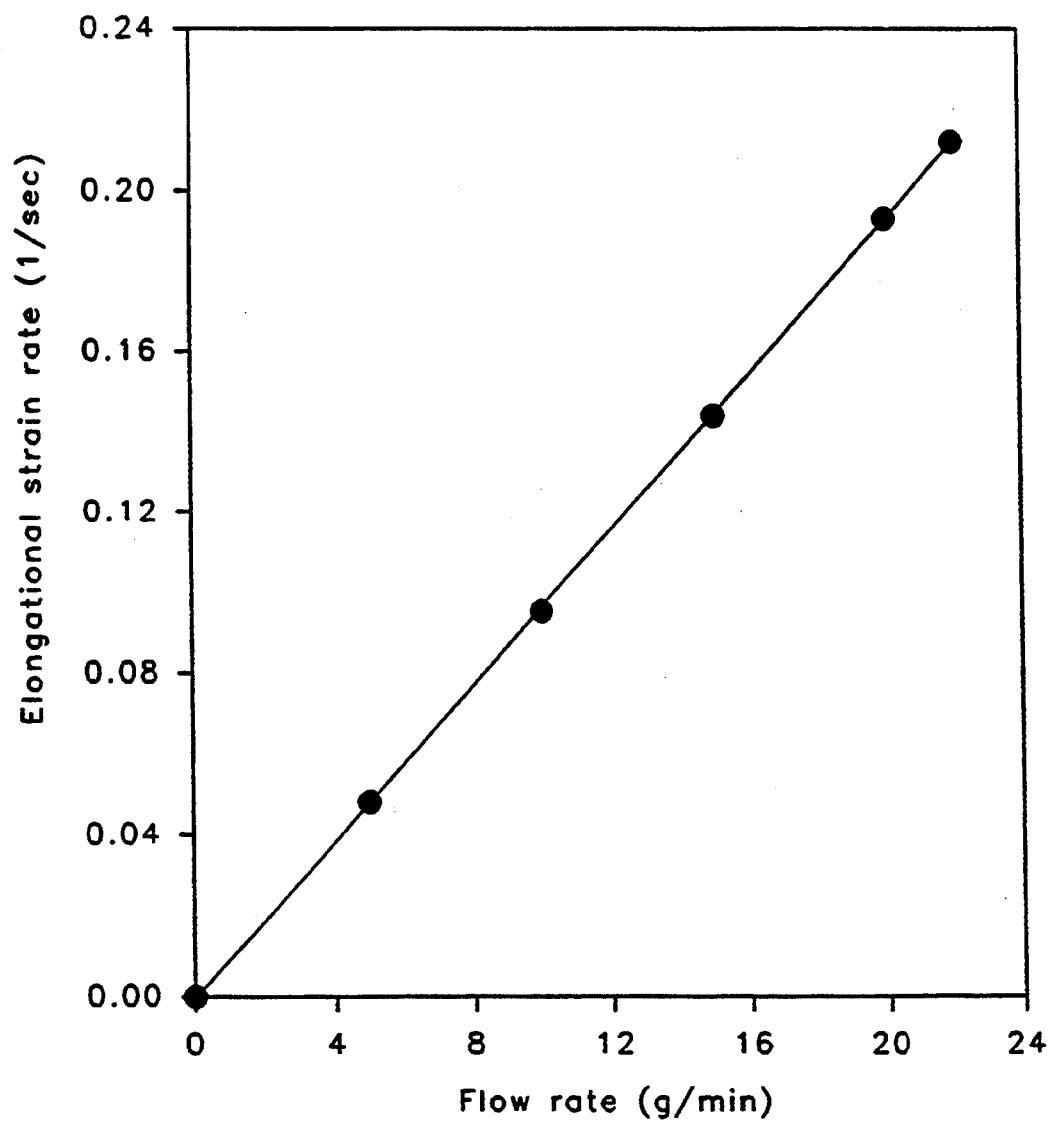
FIG. 9 illustrates elongational strain rate as a function of mass flow rate for five data sets.

Using the modified hyperbolic die, the data represented in FIGS. 8 and 9 were obtained. In FIG. 8 the measured velocity of the particles is plotted as a function of position downstream in the hyperbolic section of the die for five different volumetric flow rates. As this data indicates, the velocity is a linear function of distance down channel, as expected. As illustrated in FIG. 9, when these five data sets were used to calculate elongational strain rate as a function of mass flow rate, a linear dependence was observed, as expected. Thus in a hyperbolic die, the elongational strain rate can be controlled by the varying the mass flow rate. The measurements then needed to calculate elongational viscosity are then the pressure both upstream and downstream of the converging section, and an end and/or entrance correction factor, similar to those known in the art for a capillary shear rheometer.

The velocities of aluminum tracer particles in the melt were determined using a specially designed, side viewing die, and a video system with an image analyzer. The die was fed by two extruders, each discharging through a separate gear pump: the core melt from a Berstorff 35 mm counter rotating, intermeshing twin screw extruder, and the skin from a Brabender ¾ inch single screw extruder.

Although the examples described above used a visual observation system to demonstrate the validity of the concept, a laboratory rheometer would not ordinarily need to be so configured. A laboratory rheometer would need to measure accurately the pressure drop, the volumetric flow rate, and skin/core ratio over the measurement section to obtain stress versus elongational strain rates for the core material. In the simplest form, these measurements could be taken with a device similar to a capillary shear rheometer, but with a die having a controlled convergence section instead of a capillary, and having an appropriate fluid as a skin layer. This invention could also be used in an on-line rheometer, operating either continuously or in a batch mode, on a side stream from an industrial melt or other flow.

In such an industrial application, after providing for lubricated flow in an axially symmetric semi-hyperbolic converging section, the following parameters would be measured or otherwise known: L, the centerline length of the converging section; $A_e$, the cross sectional area of the core at the exit; $A_i$, the cross sectional area of the core at the entrance (which may not be needed in all cases, depending on the simplifying geometrical assumptions made); $\Delta P$, the pressure drop in the converging section; Q, the volumetric flow rate of the core, and $\eta$, the density of the core material. After making simplifying geometric assumptions, the elongational viscosity as a function of these parameters is then:

$$\eta_{ec} = \frac{3}{2} \left( \frac{\Delta P}{Q} A_e L - \frac{\rho Q L}{2 A_e} \right) \quad (38)$$

In a two-dimensional planar flow, the elongational viscosity as a function of the same parameters is as follows:

$$\eta_{ep} = 2 L A_e \frac{\Delta P}{Q} - \frac{\rho Q L}{2 A_e} \quad (39)$$

These equations may be written in the following general form:

$$\eta_e = a L A_e \frac{\Delta P}{Q} - b \frac{\rho Q L}{A_e} \quad (40)$$

where, for example, a is 2 for planar flow and 3/2 for axially symmetric flow; and b is ½ for planar flow and ¾ for axially symmetric flow (with the simplifying geometric assumptions). The values of a and b can be derived from a particular die geometry, including other geometries as discussed further below.

Those of skill in the art will recognize that the converging section of the die could be designed with a shape other than a strictly hyperbolic or semi-hyperbolic shape, so long as the cross-sectional area (or distance) in the converging section converged at the same rate. For example, in the planar case one side could be hyperbolic, and the other side flat; the distance between the sides still decreases hyperbolically. Or a sine-wave could be added to one face, and subtracted from the other. In the axially symmetric case, instead of a rotated semi-hyperboloid, one might use half of such a semi-hyperboloid, in which a flat plane including the axis of symmetry cuts the semi-hyperboloid in two. Another alternative, in which biaxial flow is measured, is flow in a cylinder past a mandril, where both the cylinder and the mandril have semi-hyperbolic shapes converging towards one another, and the flow is in the direction away from the "neck" of the semi-hyperboloids. This may be visualized as similar in some sense to the flow of air through a muted trumpet. Other examples of such alternatives will readily occur to one of ordinary skill in the art. As used in the claims, a "semi-hyperbolic" shape is one whose cross-sectional area decreases in the direction of flow at the same rate as does an axially symmetric shape which is purely semi-hyperbolic, thus encompassing all of the various alternatives described above; a different way to phrase the same concept is to say that the flow velocity increases linearly with length in the direction of the flow, and that the cross-sectional area decreases proportionately.

A different shape of die, which will also measure biaxial flow at a constant elongational strain rate along both axes, is one in which the flow converges hyperbolically along the x-axis as the fluid flows in the direction of the z-axis, while simultaneously diverging hyperbolically along the y-axis.

As used in the claims, the term "die" is not intended to have any specialized meaning; rather, it is intended to refer to a portion of the measuring apparatus which causes converging flow of the fluid, particularly converging flow through a hyperbolic or semi-hyperbolic shape.

Additional Details on Experimental Examples

A coextrusion system was used to obtain elongational flow in the core and to measure the elongational viscosity. The core extruder was a twin screw, co-rotating, intermeshing laboratory extruder ZE 25 manufactured by Berstorff Corporation. This extruder had two 25 mm diameter screws and a 21.5 mm center-to-center distance. The sections of the screw had different shapes of elements for conveying, kneading, and mixing. The elements were interchangeable, providing flexibility when using the extruder for different purposes and polymers. The power of the motor supplied with the extruder was 10.5 KW, and the maximum speed was 50 rpm. There were six 2.1 KW heaters along the length of the barrel, controlled by Eurotherm Corporation digital controllers (model 808 or 847) which communicated with a computer. The five main heaters also had cooling fans which were rated at 73 watts and 220 volts.

The skin extruder was a single screw extruder manufactured by Brabender Instrument Incorporated. This extruder had a 19 nun diameter screw with a length-to-diameter ratio of 20:1, and a compression ratio of 4:1. It included a 1.12 kW 220 volt model PL-V 150 motor with a maximum speed of 2400 rpm, and a gear reduction box with a reduction ratio of 20.4:1. The speed controller for the motor was a Fincor model 2400 MK II DC motor controller manufactured by Fincor Incom International Incorporated. Brabender Instruments Company supplied the two heaters on the single screw extruder, each with a rating of 800 watts, and operated on 240 volts.

A high pressure Zenith gear pump distributed by Parker Hannifin Corporation was used as the core gear pump. The capacity of this pump was 1,752 cc/rev, and it was designed to endure a high outlet pressure up to 70,000 kPa. Driving the core gear pump was a 100 volt, 0.37 kW DC motor manufactured by Pacific Scientific with a maximum rpm of 1800. A 10:1 reduction box reduced the motor's speed. The controller for the motor was a Zenith Nichols controller with an rpm range from 3.6 to 72. A 1 kW box-type heater, specially designed by Parker Hannifin Corporation, heated the core gear pump.

The gear pump for the skin polymer was a Zenith gear pump with a capacity of 0.297 cc/rev. The capacity of the skin gear pump was lower than that for the core gear pump because the flow rate of the skin polymer was about one-tenth that of the core polymer. A 100 volt, 0.19 kW DC motor with a maximum rotation of 1,725 rpm manufactured by General Electric Corporation drove the skin gear pump. The gear reducer box had a reduction ratio of 5:1. Emerson Electric Corporation supplied the controller for the motor. A met al box which was heated by two 500 watt cartridge heaters surrounded the gear pump.

A special die was used to allow observation of the flow, in order to demonstrate the validity of the concept. In a typical industrial application, a simpler conical die or insert would be preferred instead. Observation would be more difficult, but would not be needed now that the concept has been proven. The die used in this experiment was manufactured in-house. It was made of 416 stainless steel with a length of 178 mm, a width of 66 mm, and a thickness of 72.4 mm. Its flow channel had a length of 132 mm, a width of 25.4 mm and a height of 17.8 The die could be divided into two symmetrical parts, to be opened and cleaned as necessary. Bolts held the two parts of the die together. The shape of the converging section could be changed by replaceable inserts, held in the die by two hexagonal sockethead bolts. The inserts used in this study were made of 316 stainless steel. One set of inserts was manufactured by a local commercial machine shop.

The complete flow channel of the die could be viewed through either of two glass windows, one on each side of the die. The glass windows were made from a high pressure Macbeth gage glass manufactured by Corning Glass Works, and held in the die by twelve bolts. Corning Glass originally designed this borosilicate glass for use in armored-type liquid level gages to provide a high-strength tempered glass with a high degree of visibility. The glass piece had a length of 139.7 mm, a width of 33 mm, and a thickness of 17.3 mm; its maximum recommended working pressure was 35,000 kPa.

The die was heated by two 1,600 watt plate heaters from Industrial Heater Company. A model TPT 432 A-10M-6/18 transducer distributed by Dynisco measured the pressure and temperature of the polymer inside the die. The range of the pressure transducer was 70,000 kPa, and the maximum diaphragm temperature was 400° C. This transducer came in direct contact with the polymer melt.

The die often needed to be disassembled or re-assembled to change the inserts defining the converging shape, or to clean contaminants interfering with optical observation through the glass window.

Before the die was disassembled, it was heated above the melting temperature of the polymer to maintain the polymer in a molten state throughout the disassembling and initial cleaning processes. Once the polymer solidified, the die had to be heated again; otherwise, it was very difficult to disassemble. Because it was hard to clean all the polymer melt before it solidified, it had to be heated above the melting temperature while being continuously cleaned. Some liquid chemicals were tried to dissolve the polymer, but none were satisfactory. However, the commercial oven cleaner "PRIDE," made by Johnson Wax, would dissolve the carbonized polymer.

When the die was assembled, a torque wrench was used to tighten the bolts uniformly, with a torque of 110 N-m for the glass window supporting block, and 160 N-m for the main die block. The bolts were tightened in a symmetrical order for force balance. After the die was assembled, it was heated to the normal processing temperature, and all the bolts were tightened again to account for any unequal thermal expansion.

When the coextrusion system was ready to start, the motors for the extruder and for the gear pump were not turned on until the polymer inside the flow line was completely melted. The polymer inside the die took longer to melt than that inside the extruder or the intermediate pipe between the gear pump and the die, because it took some time to heat the die block itself. Hence, only the die heater was turned on initially. After about 2 hours the polymer inside the die had completely melted. The molten state could be visually confirmed through the glass window, because the polymer became transparent when molten.

When the polymer inside the die had melted, the skin and the core extruder heaters, gear pump heaters, and the heater for the intermediate pipe were turned on. If the polymer in the intermediate pipe melted faster than that in the die, the pressure in the die could become very high (up to 10,000 kPa) due to volume expansion. If, on the other hand, the polymer in the die was previously molten, a portion of the polymer melt simply discharged through the die exit.

The die temperature was set at 190° C., and the temperature of the intermediate pipe was set at 200° C. The extruder temperature and the gear pump temperature for the core polymer were set at 190° C., and those for the skin polymer were set at 170° C. Approximately 4 hours were needed for the system to reach thermal equilibrium.

Once thermal equilibrium was reached, the skin gear pump was started, and then the skin extruder. The gear pump rpm was fixed at the desired throughput rate, and the rpm of the skin extruder was adjusted such that the extruder tip pressure stayed between 3,500–7000 kPa. At least 30 minutes were allowed for the skin polymer to fill the pipe. After the intermediate pipe was filled with the skin polymer, the core gear pump was started; then both the core extruder and the chip feeder for the core polymer were started. The pressure of the core extruder tip was maintained at least at 3,500 kPa to push the polymer melt to the gear pump and to accurately meter through it. The extruder rpm and the chip feeding rate were adjusted to keep the pressure between 5,000 and 6,000 kPa.

When the polymer began flowing from the die, the take-up device was started. The speed of the take-up device was adjusted to sustain the extrudate properly. The take-up device did not pull or draw the extrudate, but merely helped it keep a uniform shape.

Two experiments were performed with the glass windows: determination of the interface position between the skin and core polymers, and (2) measurement of the velocity of the polymer melt in the converging section.

The interface position could be observed during the coextrusion process when the core polymer was colored by a blue dye. A concentration of 0.02 weight percent of Disperse Blue 56 dye was mixed with the core polymer chips fed into the core extruder. The total flow rate was 5 g/min, and the core/skin flow rate ratio was 9:1. After about an hour, the colored core polymer could be seen through the glass window and the interface position could be clearly distinguished. Images of the interface were analyzed using the "JAVA" image analysis software developed by Jandel Scientific. These procedures were repeated for core/skin flow rate ratios of 8:2 and 7:3.

The velocity of the core polymer melt in the converging section could also be measured through the glass windows. Aluminum plates with a size of about 0.1 mm × 1 mm × 1 mm served as tracers. The tracers were mixed with the core polymer chips before feeding into the core extruder. Because the aluminum tracers were very soft, they passed through the gear pump without damaging it. When they reached the die they could be seen through the glass windows, and the image was recorded on video tape for further analysis.

The velocity was measured at three different x-positions of the converging section with the JAVA software. The three locations for the linear converging die were at 0.6 mm, 20.8 mm, and 40.9 mm, respectively; and the locations for the hyperbolic converging die were at 10.7 mm, 20.8 mm, and 40.9 mm; respectively, from the beginning of the converging section. An image was captured just before these measurement positions, and just after them so that the locations of the tracers could be accurately recorded. An internal clock in the video recorder was used to measure the elapsed time.

The two polymer melt streams of polypropylene and polyethylene were joined after being separately fed through separate gear pumps. It was initially confirmed that the core polymer was properly encapsulated by the skin polymer, to be sure that the two polymers were not mixing. When the blue pigment was mixed with the core polymer, the interface was clearly visible. The pigment could be mixed with either the core or the skin polymer, but the interface was more clearly visible when the die was in the core polymer.

It was observed that the skin polymer formed the upper and lower layers, and that the core polymer was successfully encapsulated by the skin polymer. It was noticed that the streamline did not deform, and that the two polymers did not mix. The thickness of the skin layer increased as the flow rate of the core polymer decreased.

When the core polymer was fed first and the skin polymer was fed next, the skin polymer could not successfully encapsulate the core polymer. But when the skin polymer was extruded first and then the core polymer, the skin polymer would encapsulated the core polymer.

The viscosity ratio of polypropylene/polyethylene used in this study was about 100; hence, the core polymer was theoretically predicted to be in essentially elongational flow. This prediction was verified by measurements of the velocity of the core polymer with tracer particles. The experimental results agreed very well with the theoretical prediction, and it was noted that the velocity in the core did not change with location in the width direction. The skin polymer contained most of the shearing gradient; hence, the core polymer melt was essentially in a pure elongational flow region.

The elongational strain rate was measured experimentally using the modified hyperbolic converging die. First, the velocities of the polymer melt were measured at five different positions in the converging section, and then the elongational strain rate was calculated.

To obtain the elongational strain rate, velocities were measured at different x-positions. As the polymer melt moved toward the exit of the die, the velocity increased linearly, and increased as the flow rate increased. The elongational strain rate increased linearly with the flow rate.

The pressure was found to increase with the flow rate as expected, but not linearly. The calculated elongational viscosity was seen to decrease with increased elongational strain rate. The polypropylene used in this experiment showed strain thinning behavior.

To avoid instabilities at the interface between the skin and the core layer, it is preferable to operate in such a fashion that the core dominates the flow and the pressure drop. Using a core/skin viscosity ratio of at least about 100 contributes to this core dominance. There could nevertheless be a combination of die geometries and flow rates in which flow instabilities would tend to occur at the interface. In such a case, the pressure readings would develop more variation, and the physical appearance of the interface in the extrudate would be uneven. Instabilities can be avoided by operating in one of two regions: either at flow rates well below and viscosity ratios well above the onset of instabilities, or at flow rates well above that onset. In the first case the skin layer could even develop a local velocity maximum between the wall and the interface, because the flow is dominated by the resistance of the core to elongation. As a result the skin is, in effect, trying to pull the core along instead of exerting a retarding force. In the second case, if the flow rate is well above the onset of instabilities, then slip at the interface can occur, and the core behaves as a plug slipping past the skin layer.

All references cited in this specification are hereby incorporated by reference ill their entirety.

I claim:

1. A method for measuring the elongational viscosity $\eta_e$ of a fluid, comprising the steps of:
   (a) flowing the fluid through a die, at least a portion of which die comprises a semi-hyperbolically shaped, axially symmetric section, wherein said flowing is lubricated, whereby the fluid undergoes substantially pure elongational flow and substantially no shear flow in the semi-hyperbolically shaped section;
   (b) measuring the pressure drop $\Delta P$ of the fluid as it flows through the semi-hyperbolically shaped section; and
   (c) calculating the elongational viscosity $\eta_e$ from a relationship equivalent to the form $$\eta_e = a L A_e \frac{\Delta P}{Q} - b \frac{\rho Q L}{A_e}$$

wherein a and b are constants determined by the shape of the die, L is the centerline length of the semi-hyperbolically shaped section, $A_e$ is the cross sectional area of the fluid as the fluid exits the semi-hyperbolically shaped section, ΔP is the pressure drop of the fluid in the semi-hyperbolically shaped section, Q is the volumetric flow rate of the fluid, and $\eta$ is the density of the fluid.

2. A method as recited in claim 1, wherein the fluid comprises a polymer melt, a polymer solution, or a food product.

3. A method as recited in claim 1, wherein said flowing is lubricated by a second, lower-viscosity fluid.

4. A method for measuring the elongational viscosity $\eta_e$ of a fluid, comprising the steps of:
   (a) flowing the fluid through a die, at least a portion of which die converges hyperbolically in a first direction, while diverging in a perpendicular, second direction, wherein said flowing is lubricated, whereby the fluid undergoes substantially pure elongational, biaxial flow and substantially no shear flow in said portion of said die;
   (b) measuring the pressure drop ΔP of the fluid as it flows through said portion of said die; and
   (c) calculating the elongational viscosity $\eta_e$ from a relationship equivalent to the form $$\eta_e = a\, LA_e \frac{\Delta P}{Q} - b\frac{\rho Q L}{A_e}$$

wherein a and b are constants determined by the shape of the die, L is the centerline length of the said portion of said die, $A_e$ is the cross sectional area of the fluid as the fluid exits said portion of said die, ΔP is the pressure drop of the fluid in said portion of said die, Q is the volumetric flow rate of the fluid, and $\rho$ is the density of the fluid.

5. A rheometer for measuring the elongational viscosity of a fluid, comprising:
   (a) a die, wherein at least a portion of said die is semi-hyperbolic and axially symmetric, or wherein at least a portion of said die converges hyperbolically in a first direction, while diverging in a perpendicular, second direction;
   (b) means for lubricated flowing of the fluid through the die.

6. A rheometer as recited in claim 5, additionally comprising:
   (a) means for measuring the pressure drop of the fluid as it flows through said die; and
   (b) means for measuring the volumetric flow rate of the fluid as it flows through said die.

7. A rheometer as recited in claim 6, wherein at least a portion of said die is semi-hyperbolic and axially symmetric.

8. A rheometer as recited in claim 6, wherein at least a portion of said die converges hyperbolically in a first direction, while diverging in a perpendicular, second direction.

* * * * *